(12) United States Patent
Rath et al.

(10) Patent No.: US 9,538,749 B2
(45) Date of Patent: Jan. 10, 2017

(54) METHODS FOR INCREASING OIL PALM YIELD

(71) Applicant: Valent BioSciences Corporation, Libertyville, IL (US)

(72) Inventors: Andrew Rath, Underwood (AU); Peter D. Petracek, Grayslake, IL (US); Gregory D. Venburg, Deerfield, IL (US); Warren E. Shafer, Libertyville, IL (US); Max G. Villalobos Acuña, Alajuela (CR)

(73) Assignee: Valent BioSciences Corporation, Libertyville, IL (US)

( * ) Notice: Subject to any disclaimer, the term of this patent is extended or adjusted under 35 U.S.C. 154(b) by 0 days.

(21) Appl. No.: 14/708,625

(22) Filed: May 11, 2015

(65) Prior Publication Data

US 2015/0320040 A1 Nov. 12, 2015

Related U.S. Application Data

(60) Provisional application No. 61/991,779, filed on May 12, 2014.

(51) Int. Cl.
| | |
|---|---|
| *A01N 27/00* | (2006.01) |
| *A01N 53/00* | (2006.01) |
| *A01N 37/44* | (2006.01) |
| *A01N 37/10* | (2006.01) |
| *A01N 43/90* | (2006.01) |

(52) U.S. Cl.
CPC .............. *A01N 27/00* (2013.01); *A01N 37/10* (2013.01); *A01N 37/44* (2013.01); *A01N 43/90* (2013.01); *A01N 53/00* (2013.01)

(58) Field of Classification Search
CPC ........ A01N 27/00; A01N 37/44; A01N 43/90; A01N 37/10; A01N 53/00
See application file for complete search history.

(56) References Cited

U.S. PATENT DOCUMENTS

| 6,087,149 A | 7/2000 | Tsutsumi et al. |
| 8,163,244 B2 | 4/2012 | Yoo et al. |
| 8,314,051 B2 | 11/2012 | Yoo et al. |
| 8,656,638 B2 | 2/2014 | Davis et al. |
| 2007/0265166 A1 | 11/2007 | Bardella et al. |
| 2011/0318470 A1 | 12/2011 | Grossmann et al. |
| 2012/0130104 A1 | 5/2012 | Yoo et al. |
| 2013/0281296 A1 | 10/2013 | Stevenson et al. |
| 2013/0298290 A1 | 11/2013 | Haas et al. |
| 2014/0017134 A1 | 1/2014 | Yoo et al. |
| 2015/0250168 A1 | 9/2015 | Rath et al. |

FOREIGN PATENT DOCUMENTS

WO WO 2011/161132 12/2011

OTHER PUBLICATIONS

International Search Report and Written Opinion issued Jul. 28, 2015 in corresponding PCT Application No. PCT/US2015/030136.
Nualwijit et al. "Ripening delay and reduction of free fatty acids of oil palm fruit in response to 1-methylcyclopropene", Acta Hortic. (ISHS) 1011:343-349.
UNEP Global Environmental Alert Service (GEAS) "Oil palm plantations: threats and opportunities for tropical ecosystems", Dec. 2011.
Chan et al., "Effects of growth regulators on fruit abscission in oil palm, Elaeis guineensis" Ann. appl. Biol. (1972), 71, pp. 243-249.
Tranbarger et al., "Regulatory mechanisms underlying oil palm fruit mesocarp maturation, ripening, and functional specialization in lipid and carotenoid metabolism", Plant Physiology, Jun. 2011, vol. 156, pp. 564-584.
Blankenship et al. "1-Methylcyclopropene: a review" Postharvest Biology and Technology 28 (2003) pp. 1-25.

*Primary Examiner* — John Pak
*Assistant Examiner* — Andriae M Holt
(74) *Attorney, Agent, or Firm* — Wood, Phillips, Katz, Clark & Mortimer

(57) ABSTRACT

The present invention is directed to methods of using 1-methylcyclopropene (1-MCP) on oil palm before harvest of the oil palm fruit to increase oil production.

12 Claims, No Drawings

METHODS FOR INCREASING OIL PALM YIELD

FIELD OF THE INVENTION

The present invention is directed to methods of using 1-methylcyclopropene (1-MCP) on oil palm prior to harvest of the oil palm fruit to increase oil production.

BACKGROUND OF THE INVENTION

Oil palms (*Elaeis guineensis, Elaeis oleifera*, or a cross thereof) are palms that are grown to produce oil. Oil palms grow up to 20 meters tall. Their mature fruit are reddish-orange in color and about the size of a plum. The fruits grow in large bunches which grow around the palm. The time from pollination of the flowers to maturation of the fruit is about five to six months. Oil palms produce bunches year-round and the fruits are harvested as they reach maturity.

The oil palm's fruit consists of a fleshy outer layer that surrounds a palm kernel. Oil is extracted from the pulp of the fleshy outer layer and from the kernel. Oil palm is an important crop for vegetable oil production and is grown on about 15 million hectares worldwide (UNEP Global Environmental Alert Service, December 2011). The demand for palm oil is expected to double by 2020.

To meet the increasing demand for palm oil and improve efficiency, agronomic methods such as tree spacing, increased planting, fertilization, and irrigation as well as genetic improvement have been developed to optimize oil production (Corley, R. H. V. and P. B. Tinker, 2003, The Oil Palm, 4$^{th}$ edition, New York, John Wiley and Sons, 590 pp). There is still a need, however, for methods to increase production of currently planted oil palms. There is also still a need to increase oil production in order to maximize the oil production of the plants produced through genetic improvement. Further, there is a need to increase oil production of the palms managed by spacing, increased planting, fertilization, and irrigation.

Ethylene is a two carbon gaseous hydrocarbon molecule that acts as a regulator of plant growth and development. Ethylene plays important roles in many physiological processes through the lifecycle of plants including the promotion of germination, reduction of early plant growth, increase in male flower number, abscission of flowers and fruit, and promotion of ripening (Abeles, F. A. et. al., 1992, Ethylene in Plant Biology, 2nd edition, New York, Academic Press, 414 pp).

The effect of ethylene on the oil content of oil palm fruit is not well understood, however, the available literature suggests that application of ethylene increases oil content. For example, Chan, et al. (1972, Ann. Appl. Biol. 71:243-249) showed that preharvest application of the ethylene-releasing agent ethephon (2-chloroethyl phosphonic acid) to attached bunches of oil palm fruit increased oil content by 7%. Tranbarger, et al. (2011, Plant Physiol. 156:564-584) found concomitant increase in preharvest oil content and the ethylene level generated endogenously in the oil palm fruit. These reports suggest a relationship between increased ethylene levels and increased palm oil content.

Despite showing promise as a way to increase oil content, ethylene has numerous negative effects on plants which are well known in plant physiology. For example, ethylene promotes abscission of fruits and flowers which would decrease yield and yield potential. In fruit trees and bulbs, ethylene can cause the physiological disease gummosis. Gummosis is a generalized disorder of trees in which polysaccharide gum is overproduced, exuded, and deposited on the bark. Gummosis affects water relations, promotes disease, is attractive to wood-boring insects, causes shoot death, and leads to early tree decline. Based on these effects, application (particularly repeated application) of ethylene may not provide an overall benefit in oil palm.

While there is the suggestion from literature that ethylene increases oil content, one study showed that a postharvest application of the ethylene action inhibitor 1-MCP delayed ripening of oil palm fruit and reduced oil content (Nualwijit, et al., 2013, Acta Hort. 1011: 343-350). Based on this study, it was unclear whether 1-MCP would be beneficial as a pre-harvest treatment.

Accordingly, there is a need for practical methods to increase the amount of oil that oil palm trees produce. These methods should produce more oil while not harming the oil palm and should be easy to apply to the fruit or oil palm.

SUMMARY OF THE INVENTION

Applicants unexpectedly discovered that a preharvest application of the ethylene antagonist 1-MCP resulted in increased oil yields from oil palms.

In one aspect, the invention is directed to methods of increasing the content of oil in oil palm fruits by application of 1-MCP to the oil palm fruit before the oil palm fruit is harvested.

DETAILED DESCRIPTION OF THE INVENTION

1-MCP is a gas that inhibits the activity of ethylene (Blankenship and Dole, 2003, Postharvest Biol. Technol. 28:1-25). 1-MCP is commercially used in postharvest applications to delay the ripening of apples. Applicant unexpectedly found that 1-MCP delayed oil palm fruit drop (see Example 1). In light of Applicant's recent discoveries regarding the ethylene synthesis inhibitor aminoethoxyvinylglycine's (AVG) effect on oil palm and oil content (see U.S. patent application Ser. No. 14/641,870), the delay in fruit drop due to 1-MCP suggests that the 1-MCP treated fruit will also have increased oil content. This finding is unexpected because the literature shows that ethylene increases oil in oil palm when applied before harvest thereby suggesting that application of an ethylene antagonist, such as 1-MCP, would have the opposite effect as ethylene on the oil content of oil palm. Further, at least one literature source suggested that 1-MCP reduced oil content of oil palm fruits (Nualwijit, et al.).

In one embodiment, the invention is directed to methods for increasing oil content of oil palm fruit comprising applying 1-MCP directly to oil palm fruit before the oil palm fruit is harvested.

In an embodiment, the 1-MCP is in a stabilized form such as a 1-MCP/cyclodextrin complex (see U.S. Pat. No. 6,087,149).

In another embodiment, the 1-MCP is generated in situ before application from 1-MCP precursor molecules. In a preferred embodiment, the 1-MCP precursor is selected from 3-methyl-2(5H)-furanone, 5-methyl-2(3H)-furanone (angelica lactone), 1-methyl-3-oxabicyclo[3.1.0]hexa-2,4-dione, and 3,4-dioxa-1-methyl-bicyclo[4.1.0]hepta-2,5-dione, and 1-MCP is generated via photolysis of these precursors (see U.S. Pat. No. 8,656,638 and US Patent Application Publication No. 2013/0281296). In a more preferred embodiment, the 1-MCP precursor is selected from 1-methyl-1-(methanesulfonyloxy)-2-silyl-cyclopropanes such as trans-1-methyl-1-(methanesulfonyloxy)-2-(trimethysilyl)cyclopropane, trans-1-methyl-1-(methanesulfonyloxy)-2-(dimethylbutylsilyl)cyclopropane, trans-1-methyl-1-(methanesulfonyloxy)-2-(dimethylpentylsilyl)cyclopropane, trans-1-methyl-1-(methanesulfonyloxy)-2-(dimethylhexylsilyl)cyclopropane, trans-1-methyl-1-(methanesulfonyloxy)-2-(dimethylheptylsilyl)cyclopropane, trans-1-methyl-1-(methanesulfonyloxy)-2-(dimethylphenylsilyl)cyclopropane, trans-1-methyl-1-(methanesulfonyloxy)-2-(dimethyl-p-toluoylsilyl)cyclopropane, trans-1-methyl-1-(methanesulfonyloxy)-2-(diethylmethylsilyl)cyclopropane, and 1-MCP is generated by reacting the precursor molecules with fluoride salts such as a tetraalkylammonium fluoride as described in literature (see, for example, U.S. Pat. Nos. 8,163,244 and 8,314,051, and US Patent Application Publication Nos. 2012/0130104 and 2014/0017134).

The timing of application of 1-MCP to the fruit is after the palm is sexually mature, but prior to harvest. This timing range does not include when the oil palm is a seedling. Preferably, the timing range is from initial flowering to prior to harvest. More preferably, the timing range is from just prior to initial fruit drop through early fruit drop from the most mature bunch or bunches on the oil palm. This timing corresponds to about 3 to 4 weeks before harvest to the day of harvest.

1-MCP may be applied in one treatment or via multiple treatments. In a preferred embodiment, 1-MCP is applied 1 to 8 times to a maturing fruit bunch on the palm tree. If 1-MCP is applied multiple times, the preferred frequency is 2 to 6 times with an interval of application about every 7 to 35 days. The most preferred interval of application is from about every 10 to about every 21 days.

Preferably, the dose is from about 0.02 mg to about 20 g of 1-MCP per palm per application. The more preferred dose is from about 0.2 mg to about 2 g of 1-MCP per palm per application. The most preferred 1-MCP dose is from about 2 mg to about 0.2 g per palm per application.

Adjuvants such as surfactants, humectants, stickers, spreaders, urea, oils, and salts may be incorporated in a formulation containing 1-MCP to improve performance.

In an embodiment, the concentration of 1-MCP in a 1-MCP formulation that is applied to the plant is from about 0.2 to about 33,000 ppm. Preferably, the concentration is from about 2 to about 3,300 ppm. In a more preferred embodiment, the concentration is from about 20 to about 330 ppm. In a most preferred embodiment, the concentration is from about 20 to about 200 ppm.

Preferably, the volume of the application is from about 20 to about 2000 ml of a formulation containing 1-MCP per palm plant. The most preferred volume of application is from about 100 to about 600 ml of a formulation containing 1-MCP per palm plant. Amounts within the preferred volume ranges provide adequate coverage of the fruit.

The volume of the formulation applied to each bunch on the plant can vary from about 1 to about 1000 ml of the formulation containing 1-MCP per bunch. Preferably, the volume of the formulation applied to each bunch on the plant is from about 1 to about 300 ml of the formulation containing 1-MCP per bunch. In a more preferred embodiment, the volume of the formulation applied to each bunch on the plant is from about 50 to about 150 ml of the formulation containing 1-MCP per bunch.

If there are approximately 135 oil palms per hectare of land, a preferred dose is from about 2.7 mg/ha to about 448 g/ha of 1-MCP per application. The more preferred dose is from about 27 mg/ha to about 44.8 g/ha of 1-MCP per application. The most preferred dose is from about 270 mg/ha to about 4.48 g/ha of 1-MCP per application. If the density of oil palms is greater than or less than 135 oil palms per hectare of land, then the preferred dose may be proportionally increased or decreased.

1-MCP, or a salt thereof, may be used in combination with one or more other plant growth regulators such as auxins, cytokinins, gibberellins, gibberellin antagonists, salicylic acid, methyl salicylate, methyl jasmonate, S-abscisic acid (ABA) or ABA analogs. One preferred ABA analog is 3'-methyl-S-ABA.

Auxins include but are not limited to 1-naphthyleneacetic acid (NAA), indolebutyric acid (IBA), or 2,4-dichlorophenoxyacetic acid (2,4-D). One preferred auxin is NAA.

Cytokinins include but are not limited to 6-benzyladenine (6BA), forchlorfenuron (CPPU), thidiazuron (TDZ), or kinetin. One preferred cytokinin is 6BA.

Gibberellins include but are not limited to $GA_3$ (gibberellic acid), $GA_4$, or $GA_7$, or a combination of $GA_4$ and $GA_7$ ($GA_4/GA_7$).

Gibberellin antagonists include but are not limited to daminozide, mepiquat chloride, paclobutrazol, prohexadione calcium, trinexapac-ethyl, or uniconazole-P.

1-MCP or a composition comprising 1-MCP, may be foliar applied to aerial parts of the oil palm including bunches and fronds by methods such as backpack sprayers, mist blowers, tractor or ATV-mounted sprayers or aerial application. The most preferred foliar application is targeted to the oldest bunches of fruits on the palm. 1-MCP, or a composition comprising 1-MCP, may also be applied to the ground by fumigation, drip irrigation, or fertigation with nutrients or applied by trunk or bunch injection.

As used herein, "yield" refers to the amount of oil that is produced from the oil palm.

As used herein, "prior to harvest," "before harvest," and "preharvest" all refer to a time before the bunches and their fruits are harvested from the oil palm.

Throughout the application, the singular forms "a," "an," and "the" include plural reference unless the context clearly dictates otherwise.

As used herein, all numerical values relating to amounts, weight percentages and the like are defined as "about" or "approximately" each particular value, plus or minus 10%. For example, the phrase "at least 5.0% by weight" is to be understood as "at least 4.5% to 5.5% by weight." Therefore, amounts within 10% of the claimed values are encompassed by the scope of the claims.

These representative embodiments are in no way limiting and are described solely to illustrate some aspects of the invention.

EXAMPLE

Example 1

A study was conducted in a plantation in Costa Rica to compare the effects of single bunch-directed applications of: (1) untreated control (water sprayed); (2) AVG at 500 ppm (59.5 g) active ingredient (a.i.); (3) 20 ppm (2.4 g) a.i. of 1-MCP; (4) 67 ppm (8.0 g) a.i. of 1-MCP; and (5) 200 ppm (23.8 g) a.i. of 1-MCP. Total g a.i./ha for each treatment was calculated assuming 7 bunches per palm and 170 palms per ha. In this study, AVG and 1-MCP were provided in a formulation as AVG-HC1 and 1-MCP at concentrations of 20% and 1.3%, respectively.

For each treatment, 27 palms were randomly selected covering about 15 hectares. The variety of plants used was a cross between Compact and Ghana. The plants were three years old at the time of treatment. A $CO_2$ sprayer was used to spray all treatments (100 mL/bunch) to bunches with 1 to 4 loose fruits. The time required to spray each bunch was about 8 seconds at 20 psi using a 2.0 full cone nozzle. The treatments were applied once per bunch. Four, six, four, three and ten bunches per treatment were sprayed on Feb. 6, 13, 20, 27 and Mar. 3, 2015, respectively.

Cumulative loose fruit (CLF) and cumulative loose mass (CLM) counts were determined on a daily basis for 14 days with the exception of days 2 and 9 after initial spray as measure to objectively quantify fruit abscission. An electronic balance was used to weigh all fruit. All loose fruit on the bunch, branches and on the ground was counted and weighted. The results are below in Table 1.

TABLE 1

| Treatment | Cumulative Loose Fruit | % Difference with UTC | Cumulative Loose Mass (g) | % Difference with UTC |
|---|---|---|---|---|
| UTC | 148.7 | — | 1768 | — |
| 500 ppm (59.5 g) AVG | 135.1 | 9.1 | 1630 | 7.8 |
| 20 ppm (2.4 g) 1-MCP | 138.8 | 6.7 | 1465 | 17.1 |
| 67 ppm (8.0 g) 1-MCP | 106.2 | 28.6 | 1163 | 34.2 |
| 200 ppm (23.8 g) 1-MCP | 104.7 | 29.6 | 1149 | 35.0 |

As seen in Table 1, the 20, 67 and 200 ppm 1-MCP treatments decreased cumulative loose fruit 6.7, 28.6 and 29.6 percent compared to the untreated control. Further, the 20, 67 and 200 ppm 1-MCP treatments decreased cumulative loose mass 17.1, 34.2 and 36.0 percent compared to the untreated control. These results show that 1-MCP delayed palm oil fruit drop.

We claim:

1. A method of increasing oil content of oil palm fruit comprising applying an effective amount of 1-methylcyclopropene (1-MCP) to oil palm fruit from about three weeks before the fruit is harvested to about a day before the fruit is harvested, wherein the effective amount is from about 0.02 mg to about 20 g of 1-MCP per palm per treatment.

2. The method of claim 1 wherein from about 0.2 mg to about 2 g of 1-MCP per palm is applied per treatment.

3. The method of claim 1 wherein from about 2 mg to about 0.2 g of 1-MCP per palm is applied per treatment.

4. The method of claim 1 wherein the 1-MCP is applied to the fruit 1 to 8 times.

5. The method of claim 1 wherein the 1-MCP is applied to the fruit 2 to 6 times.

6. The method of claim 1 wherein the 1-MCP is applied to the fruit about every 10 to 21 days.

7. The method of claim 1 further comprising application of at least one other plant growth regulator to the oil palm.

8. The method of claim 7 wherein the at least one plant growth regulator is selected from the group consisting of an auxin, cytokinin, gibberellin, gibberellin antagonist, salicylic acid, methyl salicylate, methyl jasmonate, S-abscisic acid and S-abscisic acid analog.

9. The method of claim 8 wherein the plant growth regulator is an auxin.

10. The method of claim 9 wherein the auxin is 1-naphthyleneacetic acid.

11. The method of claim 8 wherein the plant growth regulator is a cytokinin.

12. The method of claim 11 wherein the cytokinin is 6-benzyladenine.

* * * * *